United States Patent [19]

Fuller

[11] Patent Number: 4,715,559
[45] Date of Patent: Dec. 29, 1987

[54] APPARATUS AND METHOD FOR GLOBAL NOISE REDUCTION

[76] Inventor: Christopher R. Fuller, 312 Reynolds St. Apt. 3, Blacksburg, Va. 24060

[21] Appl. No.: 863,937

[22] Filed: May 15, 1986

[51] Int. Cl.$^4$ .............................................. A61F 11/02
[52] U.S. Cl. .................................. 244/1 N; 181/206; 381/71
[58] Field of Search ............. 244/1 N, 75 A; 181/206; 381/71, 94

[56] References Cited

U.S. PATENT DOCUMENTS

| | | | |
|---|---|---|---|
| 2,361,071 | 10/1944 | Vang | 244/75 A |
| 4,025,724 | 5/1977 | Davidson, Jr. et al. | 181/206 |
| 4,473,906 | 9/1984 | Warnaka et al. | 381/71 |
| 4,562,589 | 12/1985 | Warnaka et al. | 381/71 |
| 4,589,133 | 5/1986 | Swinbanks | 381/71 |

FOREIGN PATENT DOCUMENTS

2122052  1/1984  United Kingdom ................. 181/206

Primary Examiner—Joseph F. Peters, Jr.
Assistant Examiner—Rodney Corl
Attorney, Agent, or Firm—Mason, Fenwick & Lawrence

[57] ABSTRACT

Apparatus is disclosed for attenuating sound radiated from a vibrating surface into a control volume as comprised of a source of a control signal indicative of the amplitude and frequency content of the sound transmitted from the vibrating surface. An actuator(s) or shaker is directly connected to the vibrating surface for further vibrating the vibrating surface to induce a cancelling sound into the control volume for combining with and attenuating the transmitted sound. A sensor(s) is also disposed within the control volume for detecting the resultant sound indicative of the combination of the cancelling and the transmitted sound to provide an error signal indicative thereof. A controller in the illustrative form of a computer executing a minimization algorithm, is responsive to the error signal for adaptively modifying the control signal as to phase and amplitude, which modified signal is applied to drive the actuator(s), whereby the error signal is driven to a minimum level and the sound within the control volume is similarly attenuated. One illustrative embodiment of this invention is particularly adapted to attenuate sound within the fuselage of an aircraft, wherein the principle source of noise is derived from the aircraft's engine and propeller and is introduced through the aircraft's fuselage into the aircraft's cabin. The actuator is coupled directly to the fuselage and is energized with the control signal adaptively modified as to phase and amplitude such that the cancelling sound emanating from the actuator(s) combines with and attenuates the engine and propeller noise within the aircraft cabin.

24 Claims, 11 Drawing Figures

APPARATUS AND METHOD FOR GLOBAL NOISE REDUCTION

BACKGROUND OF THE INVENTION

1. Field of the Invention

The present invention is in the field of noise reduction and is specifically directed, in its preferred embodiment, to an apparatus and method for reducing fuselage interior noise in a propeller driven aircraft. However, the invention is also usable in noise reduction in other non-aeronautical environments.

2. Description of the Prior Art

There has been a substantial amount of work done in connection with propeller driven aircraft and, in particular, with the proposed advanced turbo-propeller (ATP) aircraft due to their inherent high fuel efficiency. A drawback of such ATP aircraft resides in the high levels of sound within the aircraft's cabin due to the higher tip velocities of their rotating propellers and the large amplitude vibrations induced in the wings by engine vibration harmonics and propeller wakes. Hence, the prior art has been concerned with reduced noise transmitted through the fuselage and into the cabin interiors of such aircraft.

Investigations as reported in "Characteristics of Propeller Noise on an Aircraft Fuselage Related to Interior Noise Transmission," by J. S. Mixson et al., *AAIA* 79-0646, 1979, and in "Development and Validation of Preliminary Analytical Models for Aircraft Interior Noise Prediction," by L. D. Pope et al., *J. Sound Vib.*, 82(4), 1982, conclude that aircraft noise could best be reduced by the use of panels having characteristics of mass, stiffness and damping, which minimize the transmission of sound therethrough, when installed in an aircraft fuselage. Such panels are passive in nature and only work well for high frequencies. Since propeller noise will vary in frequency in accordance with the aircraft operating conditions, such panels do not provide for full-time noise reduction in the low frequency region where the major noise of ATP's resides. Another approach to aircraft noise reduction is the use of absorbent damping material placed in the inside of the aircraft fuselage for damping out the acoustic field. In general, propeller noise is of a very low frequency in the order of 100 to 250 Hz, having a corresponding long wavelength. This absorbent damping is ineffective against such long wavelengths, working well only at high frequencies. The disadvantages associated with these solutions are thus the weight added to the aircraft, plus the lack of low frequency attenuation.

Another approach to the problem of noise reduction in fuselage interiors of aircraft has been to use tuned mechanical vibrators. In such installations, small mass springs are attached to the fuselage surface at various interior locations. These springs have resonant frequencies which cause them to vibrate in response to being subjected to sound at a particular frequency. Such systems are not active and only work at one single frequency. Moreover, such systems do not provide for good global attenuation unless many springs are employed, thus adding weight to the aircraft; such springs are totally useless when the sound in the aircraft cabin operates at frequencies other than their one design frequency, and also tend to be fragile.

The publication entitled "Propeller Signatures and their Use" by J. F. Johnson et al., *AIAA*, 80-1035, 1980, discusses the synchrophasing of propeller blades to reduce aircraft noise in propeller driven aircraft. Synchrophasing involves the adjustment of the relative rotational phase of different propellers on the aircraft to effect noise reduction. Synchrophasing operates to effect a noise reduction over a reasonable volume of the order of 8 dB in sound pressure level. Apparently, synchrophasing provides significant noise rejection rather than a redistribution of the acoustic energy within the aircraft cabin, implying that active methods which affect fuselage vibration will be successful in providing global attenuation inside the aircraft cabin.

An active noise cancellation system is described for an ATP aircraft in a NASA report number CR172386 entitled "Active Attenuation of Propeller Blade Passage Noise," by Zalas et al. This active noise cancellation system for the interior of an aircraft, includes an input sensor for providing a signal indicative of the rotational velocity of the aircraft's propeller or the frequency content of the propeller noise. The input sensor may include a synchrophasor signal from the aircraft engines, an accelerometer coupled to the fuselage wall of the aircraft, an interior microphone or an exterior microphone. The input signal is applied to a controller in the form of a computer for executing a modified Widrow-Hoff least means squared (LMS) algorithm for adjusting the amplitude and phase of the signal applied to a loudspeaker or loudspeakers disposed within the aircraft cabin, to minimize the sound level at a particular location(s) with the aircraft cabin. The controller output is amplified before being applied to the loudspeaker(s), which output a sound of appropriate phase and amplitude to cancel the objectionable noise. An error sensor is disposed within the aircraft fuselage to apply an error signal proportional to the residual noise, to the controller, which adjusts its output signal as to phase and amplitude to achieve a minimum noise level within the aircraft cabin. To achieve optimum noise cancellation, the loud speaker should be relatively small with respect to the wave length of the noise and of approximately the same size as the noise source, and further should be disposed as close to the noise source as possible. The acknowledged drawback of this system was that noise cancellation did *not* occur at positions within the interior volume of the aircraft other than where the error sensor was placed. In particular, noise cancellation occurred, wherein a single cancellation speaker was used, of less than a quarter wave length around the error sensor. This publication recognizes the limitations of this method to achieve global attenuation throughout the volume of the aircraft cabin and suggests that further studies be conducted to determine the mechanism and characteristic of sound transmission into the interior of an aircraft's fuselage to identify the points at which sound is introduced therein and to employ an array of the speakers disposed within the aircraft cabin to potentially achieve global noise reduction.

SUMMARY OF THE INVENTION

It is therefore an object of this invention to provide a new and improved sound attenuating system for globally attenuating sound throughout a control volume.

It is a further object of this invention to provide a new and improved sound attenuating system wherein the cost and weight in terms of actuators is reduced.

It is a still further object of this invention to provide a sound attenuating system for an aircraft, wherein sound reduction is effected throughout the desired portion of the aircraft's cabin and with apparatus of minimum weight and cost, as might otherwise impair the efficiency of the aircraft.

In accordance with these and other objects of the invention, there is provided apparatus for attenuating sound radiated from a vibrating surface into a control volume, comprising a source of a control signal indicative of the amplitude and frequency content of the sound radiated from the vibrating surface. An actuator or shaker is directly connected to the vibrating surface for further vibrating the vibrating surface to induce a cancelling sound into the control volume for combining with and attenuating the radiated sound. A sensor is also disposed within the control volume for detecting the resultant sound indicative of the combination of the cancelling and the radiated sound to provide an error signal indicative thereof. A controller in the illustrative form of a computer executing a minimization algorithm, is responsive to the error signal for adaptively modifying the control signal as to phase and amplitude, which modified signal is applied to drive the actuator, whereby the error signal is driven to a minimum level and the sound within the control volume is similarly attenuated.

One illustrative embodiment of this invention is particularly adapted to attenuate sound within the fuselage of an aircraft, wherein the principle source of noise is derived from the aircraft's engine and propeller and is introduced through the aircraft's fuselage into the aircraft's cabin. The actuator is coupled directly to the fuselage and is energized with the control signal adaptively modified as to phase and amplitude such that the cancelling sound emanating from the vibrating fuselage surface as driven by the actuator, combines with and attenuates the engine and propeller noise within the aircraft cabin.

BRIEF DESCRIPTION OF THE DRAWINGS

This invention may be better understood, and further advantages and uses thereof are readily apparent, when considered in view of the following detailed description of the exemplary embodiments, taken with the accompanying drawings, in which.

DESCRIPTION OF THE PREFERRED EMBODIMENTS

Figure 1A:
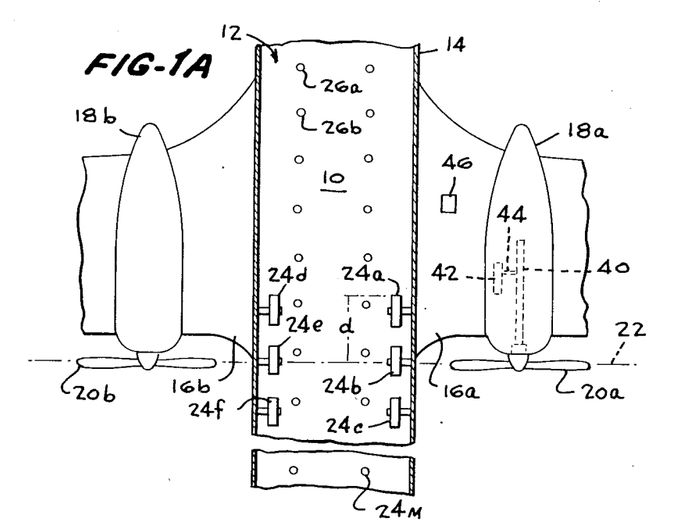
FIGS. 1A and 1B are respectively a partially broken away, top plan view and a front sectioned view of an aircraft, wherein the propellers are disposed in advance of the aircraft's wings and including the active noise reduction system of this invention to reduce the level of noise within a control volume, i.e. a part of the aircraft cabin.
Figure 1B:
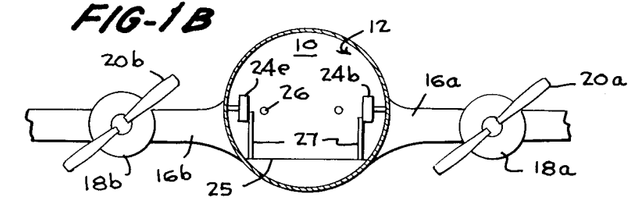

Referring now to the drawings and in particular to FIGS. 1A and B, there is shown a control volume 10 defined by a cabin of an aircraft 12, taking the form in one illustrative embodiment of this invention of an advanced turbo-propeller (ATP) aircraft, wherein a pair of propellers 20a and 20b is mounted in advance of a pair of wings 16a and 16b. The propellers 20a and 20b are disposed in a common, propeller plane 22 indicated by a dot-dash line. The propeller plane 22 intersects the aircraft cabin 12 and the control volume 10 defined thereby, as indicated in FIG. 1A. Though this invention will be explained with reference to a control volume 10 as formed by such an ATP aircraft, it is realized that the active noise reduction system of this invention could be used to control undesired noise within any control volume as disposed within a noise field radiated from a structurally vibrating surface. For example, this invention could be applied to a control volume formed by a machine cover or, on a larger scale, by a factory (or part of a factory), wherein the space (or a part of the space) within the factory walls is the control volume 10. In the illustrative embodiment as shown in FIGS. 1A and 1B, the propellers 20a and 20b are rotatively driven by a pair of engines 18a and 18b mounted upon the wings 16a and 16b, respectively. Each of the engines 18 rotatively drives a shaft 40, to which a propeller 20 is coupled. A device 42 known as a pipper is associated by a suitable coupling 44 with the shaft 40 to provide an output signal indicative of the rotational velocity of the propeller shaft 40.

An array of "m" number of microphones 26a to 26m is disposed within the aircraft cabin 12, and the microphone placement defines the control volume 10, in which noise will be minimized. In other words, the extent of the array of microphones 26 defines the extent of the control volume 10. The number and locations of the microphones 26 depends on the structure of a particular aircraft and its aircraft cabin 12. In an illustrative embodiment of this invention, the microphones 26 could be disposed in the head rests of the middle seat in each row. It is contemplated that a typical passenger aircraft may contain from 10 to 50 microphones. The wiring interconnecting the microphones 26 to an adaptive controller, as will be discussed, is concealed within the passenger seats and underneath the floor of the cabin 12. At least one actuator or shaker 24 is employed by the active noise reduction system of this invention and, in particular, is directly coupled to the fuselage 14 to induce vibrations of such phase and amplitude, within the fuselage 14 which in turn radiates cancelling sound into the aircraft cabin to interfere or combine with and to reduce the noise within the control volume 10. In the context of an ATP aircraft, the principle source of the noise within the control volume 10 originates from the propellers 20 and their engines 18, as transmitted via the wings 16 and through the fuselage 14.

The number and placement of the actuators 24 will depend upon the particular aircraft. Testing will be done upon a particular aircraft to determine the distribution of pressure variations throughout the control volume 10 and the pattern of vibrations induced within a particular fuselage 14. FIG. 1A discloses a preferred embodiment of this invention, wherein an arrangement of actuators 24 is disposed on either side of the propeller plane 22. As viewed in FIG. 1A, a first pair of actuators 24a and 24d is disposed above the propeller plane 22, a second pair of actuators 24b and 24e is disposed in the propeller plane 22, and a third pair of actuators 24c and 24f is disposed below the propeller plane 22a. Most actuators 24 are disposed within a distance "d" on either side of the propeller plane 22, where the spacing "d" is set less than the average diameter of the cross-section of the fuselage 14 as taken by the intersecting propeller plane 22.

Imperical tests have shown that the noise transmitted from the propellers 20 of an ATP aircraft enter the aircraft cabin 12 at the line of intersection between the fuselage 14 and the propeller plane 22 and radiates in either direction through the fuselage 14, being attenuated as the sound induced vibrations travel through the fuselage 14. Any actuator 24 disposed beyond the distance "d" from the propeller plane 22 is not particularly effective to further reduce the noise within the control volume 10. The actuators 24 are mounted within their own discrete housings to exert their force in an inertial manner on the fuselage 14. When an actuator 24 vibrates, it applies an impulsive force. If the actuator 24 is hanging freely, i.e. inertially, then the force that can be applied is limited by its inertial mass. In other words, the mass of the actuator 24 has to resist the movement backwards as the impulsive force is applied by the actuator 24 to the fuselage 14. If the actuator 24 is inertially mounted, the actuator mass must be made greater than the required impulse force of the actuator 24 to be exerted to the fuselage 14. Alternatively as illustrated in FIG. 1B, the housings for the actuators 24b and 24e are supported by brackets 27 directly from the floor 25 of the cabin 12, whereby the actuator's force is directly applied to the fuselage 14.

Further, the actuators 24 have sufficient mass and force so that upon being driven by an appropriate signal, they induce significant vibrations relative to propeller induced vibrations, within and traveling about the fuselage 14. The vibrating surface of the fuselage 14 radiates a cancelling sound into the control volume 10, i.e. the aircraft cabin. In an illustrative embodiment of this invention, an actuator may take the form of any one of the models VTS 50, 75 or 90 as manufacturered by Vibration Tests System of Aurora, Ohio. Typically, such models weigh in the order of 50 pounds, whereby upon being driven, the actuator 24 induces vibrations inertially in the fuselage 14.

Tests have shown that the amplitude of the vibrations induced in the fuselage 14 at the intersection line defined by the intersection line between the propeller plane 22 and the fuselage 14, fall off approximately, in accordance with a bell-shaped curve, as the vibrations travel a distance from this intersection line. At a distance of three-fourths of the diameter of the cross-section of the cabin 12 from the intersection line, the amplitude of the vibrations has fallen off approximately 20 dB.

Figure 2A:
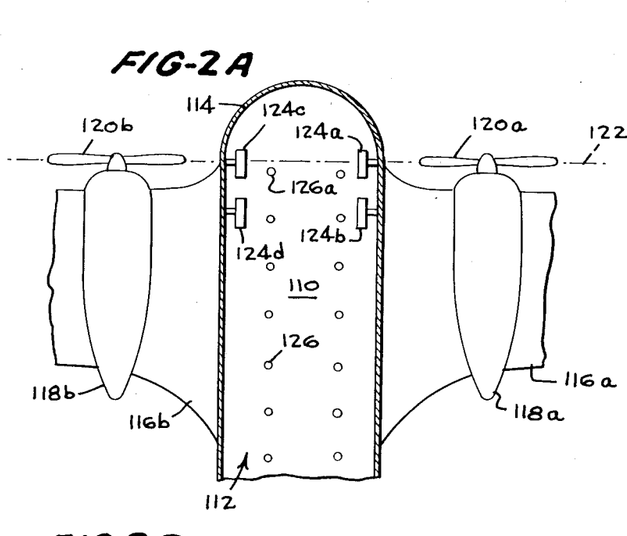
FIGS. 2A and 2B are respectively a partially broken away, top plan view and a sectioned, front view of a different configuration of aircraft, wherein the propellers are mounted rearwardly of the aircraft's tail plane section, and incorporating the active noise reduction system of this invention.
Figure 2B:
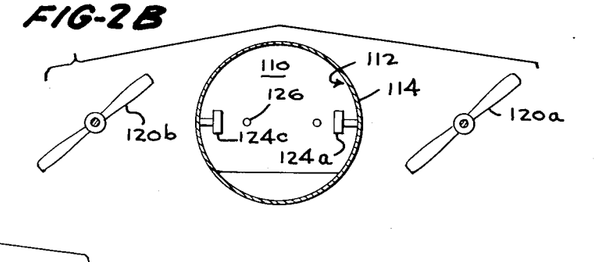

FIG. 2A shows a further embodiment of an aircraft, wherein the active noise reduction system of this invention may be incorporated. Elements of FIGS. 2A and 2B, which are similar to those of FIGS. 1A and 1B, are identified by similar numbers, but in the 100 series. The propellers 120a and 120b are mounted upon a tail plane section and, in particular, upon tails 116a and 116b, whereby the propellers 120a and 120b are oriented to push the aircraft, in a forward or downward direction as shown in FIG. 2A. The propellers 120a and 120b define the propeller plane 122, which intersects the fuselage 114 at the rear of the aircraft. In this embodiment, a first pair of shakers 124a and 124c is mounted to intersect the propeller plane 122, whereas a second set of actuators 124b and 124d is mounted at a distance forward of said propeller plane 122 less than one diameter of the cross-section of the aircraft's cabin 112.

Figure 3:
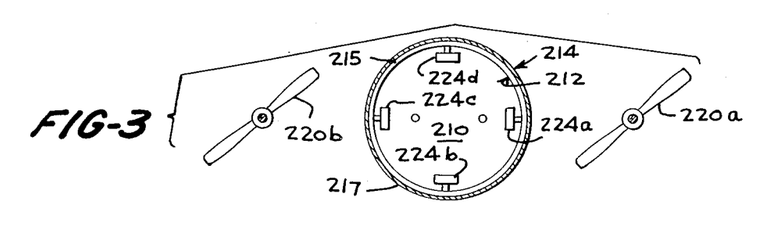
FIG. 3 is a sectioned, front view of an aircraft for receiving the active noise reduction system of this invention for driving a plurality of actuators mounted within the propeller plane.

Referring now to FIG. 3, there is shown a still further embodiment of the aircraft in which the active noise reduction system of this invention may be incorporated; in FIG. 3, elements similar to those in FIGS. 1A and 1B are identified by like numbers but in the 200 series. A plurality of actuators 224a to 224d is mounted within the propeller plane 222; each of the actuators 224a to 224d is connected to the fuselage 214. The fuselage 214 comprises, as well known in the art, a plurality of circumferential ribs 215 and a skin 217 stretched about and suitably fastened to the ribs 215. In FIG. 3, the actuators 224 are attached to one of the ribs 215; alternatively, the actuators 224 could be attached to vibrate directly the skin 217. In order to reduce the cost, as well as the weight added to the aircraft, it is contemplated that but a single actuator 224, would be attached to the fuselage 214 to attenuate noise within the control volume 210. As additional actuators 224 are added, the level of noise reduction is decreased or the range of frequencies controlled is increased, until the point of diminishing return is reached in terms of weight added to the aircraft and cost. The coupling of a transducer 224 to the circumferential rib 215 or skin 217 also increases the efficiency of the coupling to the aircraft's fuselage 214.

Referring to FIGS. 1A or 2A, sound from the propellers 20 and their engines 18 is introduced primarily along the source or propeller plane 22 into the control space 10 within the aircraft cabin 12. The fuselage 14 is substantially cylindrical in configuration. Vibrations are induced in the fuselage 14 and travel circumferentially about the fuselage 14, establishing one or more shell circumferential modes within the fuselage 14. A shell mode is a standing wave of the induced vibrations having a number of nodes equally spaced about the circumference of the fuselage 14 and a particular frequency. The number of nodes and frequency are dependent upon the structure of the fuselage 14 and the nature of the propeller radiated noise. Measurements have shown that though there may be a relatively large number of such shell modes, typically the standing waves of only three or four of such shell modes have any significant amplitude. However, further observation indicates that only one or possibly two of these shell modes are efficiently coupled to the control space 10 at a particular frequency. Thus, the total acoustic energy of the control volume 10 is dependent in any substantial manner on one or possibly two of the shell modes at a particular frequency.

The number of actuators 24 required for effective noise attenuation is dependent on the number of shell modes, which are efficiently coupled to the control volume 10, one effectively coupled shell mode requiring one actuator 24. If the noise or acoustic energy is of a single frequency corresponding to the resonance of the fuselage 14, analysis of the efficiency, i.e. modal decomposition, of the sound coupling between the fuselage 14 and the control volume 10 indicates that efficient coupling will usually only occur at one shell mode. Thus, control theory would indicate that but a single actuator 24 would be efficient to attenuate such noise of the single cavity resonant frequency. However, if the noise is of an off-resonance frequency of the fuselage 14, the modal density of the interior sound field increases such that more than one actuator 24 may be needed to minimize the noise within the control volume 10.

Further, the sound from most propellers 20 and engines 18 exhibits a plurality of dominant frequencies. Each such frequency is coupled via the source plane 22 to the control volume 10 causing one or more shell modes at each of the dominant frequencies. However, modal decomposition analysis of the coupling of the shell modes to the control volume 10 indicates that only a limited number of such shell modes will be coupled efficiently to the control volume 10 and, thus, need to be controlled. The number of actuators 24 equals the number of modes to be controlled in the control volume 10. Thus, even when a plurality of frequencies is considered, only a limited number of actuators 24 is needed to attenuate the sound within the control volume 10.

Further, the minimum number of microphones 26 required within the aircraft is determined by the number of interior accoustic modes efficiently coupled to the aircraft's fuselage 14. Each accoustic mode establishes a standing wave of a particular frequency in the control volumne 10. According to Nyquist theory, two microphones are required to unequivocally detect that accoustic mode at that frequency. Further, the spacing between a pair of microphones 26 dedicated to one acoustic mode, should be spaced apart such that at least one microphone of the pair is disposed on opposite sides of the node of the standing wave of that acoustic mode. Microphones 26 so placed are capable of detecting standing waves in the acoustic field of the control volume 10.

Though this invention is explained with reference to a control volume 10 as formed by such an ATP aircraft, it is realized that the active noise reduction system of this invention could be used to control undesired noise within any control volume as disposed within a noise field radiated from a structurally vibrating surface. For example, this invention could be applied to a control volume formed by a machine cover or, on a larger scale, by a factory (or part of a factory), wherein the space (or a part of the space) within the factory walls is the control volume. A control volume 10 may be defined within any noise radiated field and is not necessarily related to any kind of housing or envelope that may otherwise define the control volume 10 as in the embodiment of the ATP aircraft. Instead, as generally indicated above, the array of "m" microphones 26a to 26m defines the perimeter or extent of the control volume 10, dependent upon the nature of the radiated sound. Illustratively, if the control volume 10 is to be of a particular configuration, e.g. circular, the array of microphones 26a to 26m is disposed in a like configuration. The number of microphones 26 is dictated in accordance with the frequency content or modal density of the radiated noise and, in particular, upon the standing wave mode or modes that are present in the noise radiated field. The spacing between adjacent microphones 26 disposed in the array is dependent upon the standing waves present in the noise radiated field. In particular, adjacent microphones 26 of the array are spaced from each other so as to fall on opposite sides of the nodes of the highest frequency standing wave as present in the noise radiated field. If there are no standing waves in the radiated field as in free-field radiation, then the control volume 10 will be simply defined by the volume contained with an array of microphones 26. As indicated above, the output signals from the microphones 26 are used to adaptively drive actuators 26 that are coupled directly to the vibrating surface, e.g. a machine housing. As a result, the radiated noise within the control volume 10 will be significantly attenuated, whereas noise elsewhere in the field will not necessarily be affected.

Figure 4A:
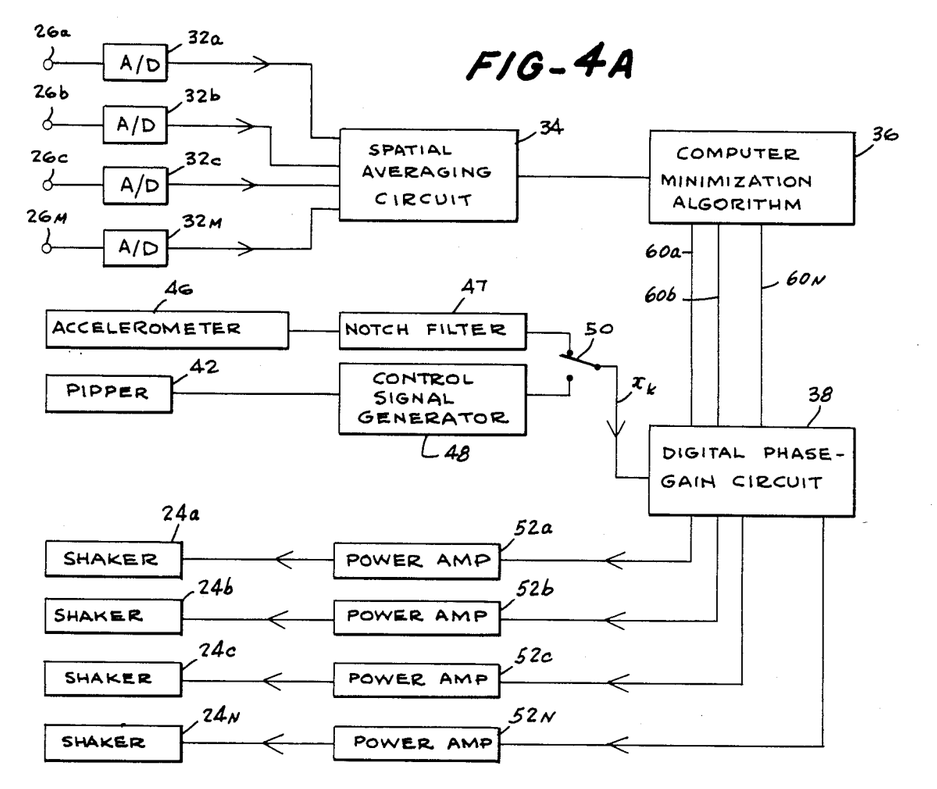
FIGS. 4A and 4B are functional block diagrams respectively of a first embodiment of the active noise reduction system for this invention, as may be incorporated into an aircraft as illustrated in any of FIGS. 1A, 1B, 2A, 2B, and 3, and particularly adapted to respond to a control signal of a single frequency set according to the dominant frequency component of the propeller's noise, and of the elements of a digital phase-gain circuit, as generally shown in FIG. 4A.

Referring now to FIG. 4A, there is shown a functional block diagram of an active noise reduction system 30 in accordance with the teachings of this invention. The purpose of this system 30 is to minimize the global noise throughout the control volume 10 to a predetermined minimum. As indicated above, the control volume 10 is that space within the aircraft cabin 12 in which it is desired to minimize the total noise or acoustic energy. The size of the control volume 10 is dependent upon the aircraft type, the propeller configuration, and the placement of the array of microphones 26, realizing that noise appearing outside of the array will be affected, but not necessarily reduced by this system 30. Global means throughout the control volume 10. This system 30 reduces globally the undesired acoustic energy or noise induced within the control volume 10; in other words, the interior noise is minimized substantially uniformly at all points within the control volume 10. This result contrasts markedly with the active noise reduction system described in the above-identified NASA Contractor Report, wherein noise cancellation or minimization was limited to a space within a quarter wavelength of that noise from the microphones.

In the context of this system 30, noise appears in the control volume 10 as oscillating pressure rarifications and compactions and is measured by the array of "m" number of microphones 26a to 26m, as shown in FIG. 4A. Each microphone 26 outputs a signal indicative of the level of noise at that microphone position proportional to the pressure difference between the rarifications and compactions. The microphone output is applied to an analog-to-digital (A/D) converter 32, which applies a digital signal to a spatial averaging circuit 34, which receives inputs from the "m" microphones 26a to 26m and obtains a mean squared indication $p_e$ of the measured squared pressure amplitude of the sum of these signals, which may be represented as:

$$p_e = \overset{M}{\underset{}{\Sigma}} \frac{p^2_{rms}}{M}, \qquad (1)$$

where "m" equals the number of microphones 26 and P equals the sum of the noise or means squared pressure signals derived from the "m" microphones 26. The output of the spatial averaging circuit 34 is proportional to the spatial average of the acoustic energy content within the control volume 10.

The noise inserted into the aircraft cabin 12 primarily originates from the propellers 22 and their engines 18.

The system 30 employs a signal source in the form of a pipper 42 or an accelerometer 46 or exterior mounted microphone to develop a control signal indicative of a single, dominant frequency component of the noise transmitted within the aircraft cabin 12. A switch 50 determines which of the pipper 42 or the accelerometer is coupled to the circuit 34. A further embodiment of this invention will be described that responds to a broad frequency band of signals. An analysis of the sound originating from the propellers 20 reveals a fundamental frequency and a number of harmonics thereof, where the frequency "f" of a harmonic order is calculated as:

$$f = N_H \cdot RPM \cdot N_B / 60 \qquad (2)$$

where NH is the harmonic order of the frequency component, RPM is the rotational velocity in revolutions per minute of the propeller 18 and $N_B$ is the number of propeller blades. For example, if $N_H$ equals 1, the frequency would be the fundamental frequency. If $N_H$ equals 2, the frequency component would be the first harmonic.

As shown in FIG. 4A, the control signal could be provided by an accelerometer 46 or an exterior microphone mounted upon the exterior of the fuselage 14 and applied to a notch filter 47 to eliminate frequency components above and below a selected frequency. Analysis of propeller noise indicates that the fundamental frequency of most propellers of typical ATP aircraft is in the range of 50 to 500 Hz. The filter output is applied by a switch 50 to a digital phase-gain circuit 38, whose operation will be explained below. Alternately, a pipper signal is derived from sensor 42. Illustratively the sensor 42 could take the form of a device coupled to measure the rotational velocity of the shaft 40, as shown in FIG. 1A. Illustratively, a magnetic sensing device could be used to sense the rotation of a magnet fixed to the shaft 40 or, alternately, a photoelectric cell could be used to sense the interruption of a light path to provide a signal of a frequency corresponding to the rotational velocity of the shaft 40 and the propeller 20 affixed thereto. Alternatively, the rotational velocity may be obtained from the synchrophaser, if fitted to the aircraft. The output of the pipper 42 is applied to a control signal generator 48, as comprised of an oscillator for generating a sine wave of a frequency corresponding to the dominant harmonic component of the propeller noise. The dominant component is determined by analysis of the engine noise to determine which of fundamental, first or second harmonic is of the highest amplitude. Thus, the control signal generator 48 outputs a sinusoidal signal of a frequency corresponding to the dominant harmonic component via the switch 50 to the digital phase-gain circuit 38.

The digital phase-gain circuit 38 splits the control signal, derived as discussed above, into "n" channels and controls the amplitude and phase of each such channel, to drive a like number "n" of actuators 24a to 24n to attenuate globally the noise within the control volume 10, as shown in FIGS. 1A and 1B. A like number "n" of power amplifiers 52a to 52n amplify the individual outputs of the digital phase-gain circuit 38 before applying them to corresponding actuators 24a to 24n. The gains of the amplifiers 52 are initially set (and then left constant) at a level so that the actuators 24 vibrate the fuselage 24 at approximately the level required. The digital phase-gain circuit 38 is capable of changing the phase and amplitude of each of its outputs in accordance with control signals developed by a computer 36 executing a minimization algorithm, illustratively a least means squared (LMS) routine as described in NASA Contractor Report 165698, entitled "An Operations Manual for the Spinning Mode Synthesizer in the Langley Aircraft Noise Reduction Laboratory," by Daniel L. Palumbo. The computer 36 executing this LMS routine controls the imaginary and real parts (i.e. amplitude and phase) of each of the "n" outputs of the digital phase-gain circuits 38, whereby the noise within the control volume 10 is globally attenuated until the output of the spatial averaging circuit 34 is minimized to a predetermined level. The actuators 24a to 24n vibrate the fuselage 14, which in turn radiates from the inner surface of the fuselage 14 a cancelling sound into the control volume 10. As indicated, the phase and amplitude of the outputs of the digital phase-gain circuit 38 are so adapted that the cancelling sounds emanating from the radiating surface, e.g. the fuselage 24, driven by the corresponding actuators 24a to 24n combine with and attenuate the engine and propeller noise transmitted into the aircraft cabin, until the resultant sound within the control volume 10 and thus the output of the spatial averaging circuit 34 is reduced to a predetermined minimum. The computer 36 calculates the difference of the output of circuit 34 and a predetermined minimum noise level to produce an error signal; the computer 36 runs the minimization algorithm to reduce this error signal to zero, or other required minimum value.

In an illustrative embodiment of this invention, the control signal generator 48 could take the form of a 810 Series Digitally Programmable Quadrature Sinewave Oscillator as manufactured by Frequency Devices Incorporated of Haverhill, Massachusetts. The power amplifiers 52a to 52n may illustratively take the form of that power amplifier manufactured by Vibration Test System of Aurora, Ohio under their model designations OVTS 45/7520, 65/7540 or 100/7550.

Figure 4B:
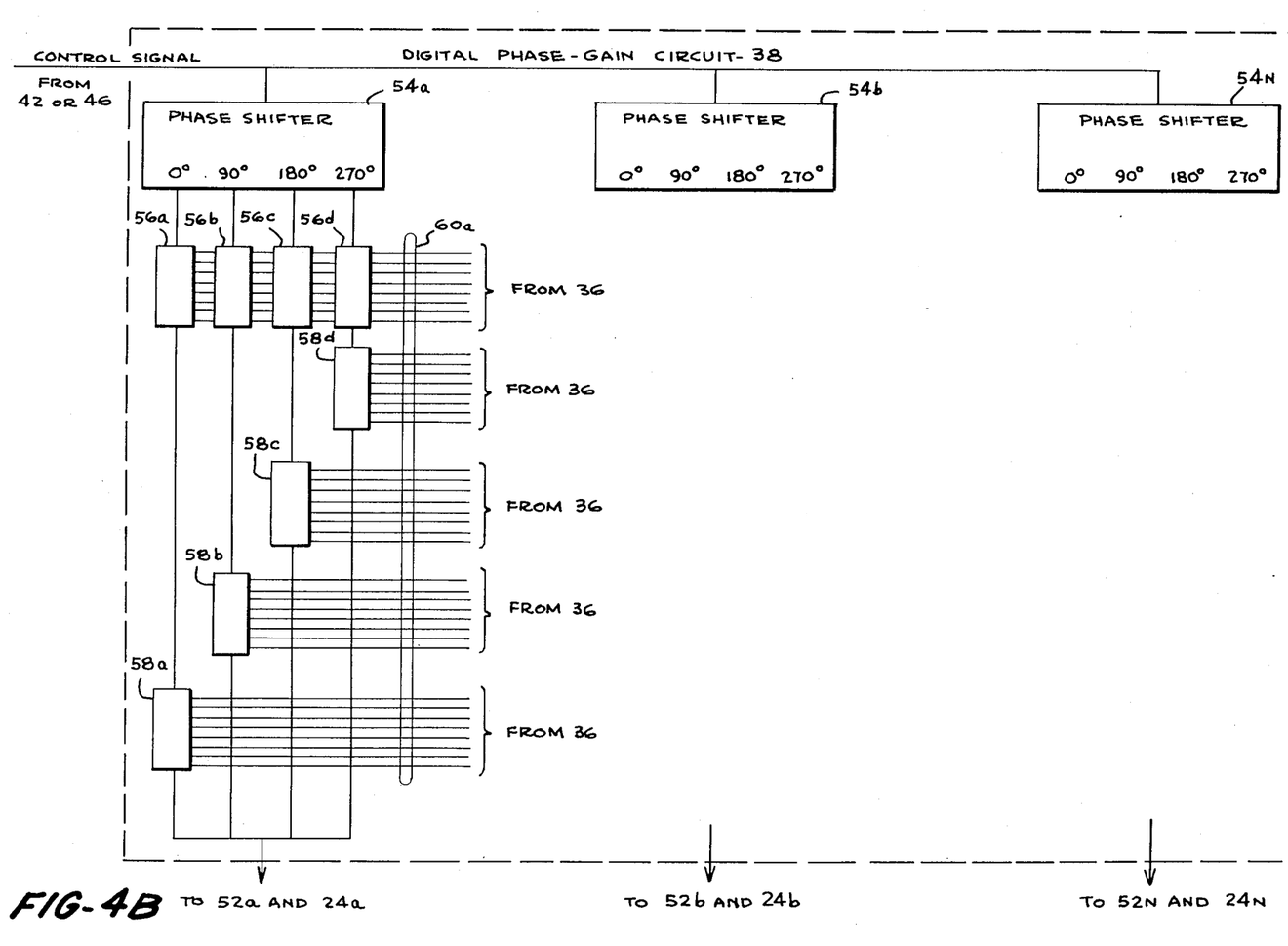

The structure of the digital phase-gain circuit 38 is more fully shown in FIG. 4B. In particular, the control signal as developed by either the pipper 42 or the accelerator 46 is applied to each of "n" phase shifters 54a to 54n. Each phase shifter 54 divides the control signal into a plurality of signals, each shifted a predetermined amount from the other, e.g. 90°. In an illustrative embodiment of this invention, the phase shifter 54 outputs signals shifted by 0°, 90°, 180° and 270° to be applied to a corresponding plurality of digitally controlled amplifiers 56a to 56d, which are controlled by the computer 36 to adjust in like fashion the amplitude of each of the outputs of the phase shifter 54. As indicated in FIGS. 4A and 4B, the computer 36 outputs via each of a plurality of "n" busses 60a to 60n an 8 bit control signal setting in common the amplitude of the output of the amplifiers 56a to 56d. Further, the phase of each output of the phase shifter 54 is individually set by a corresponding plurality of digitally controlled amplifiers 58a to 58d. As indicated in FIG. 4B, the outputs of the amplifiers 58a to 58d are summed and applied to a corresponding one of the actuators 24, whereby that actuator 24 is driven with a signal of amplitude and phase to reduce globally the noise within the control volume 10. As indicated in FIG. 4B, each of the phase shifters 54a to 54m outputs a corresponding set of 0°, 90°, 180° and 270° signals whose phase and amplitude are similarly controlled by the computer 36.

In an alternate embodiment of this invention, a single set of control lines for amplitude and phase could be applied in common to the amplifiers 56 and 58 for each of the "n" channels, whereby address signals would be applied over address lines thereto (not shown) to selectively address each amplifier 56 or 58 to set its gain before setting the gain of the next. In such an embodiment, the amplifiers 56 and 58 may illustratively take the form of that circuit as manufactured by MOTOROLA under their designation MC 1408 L-8.

Figure 5:
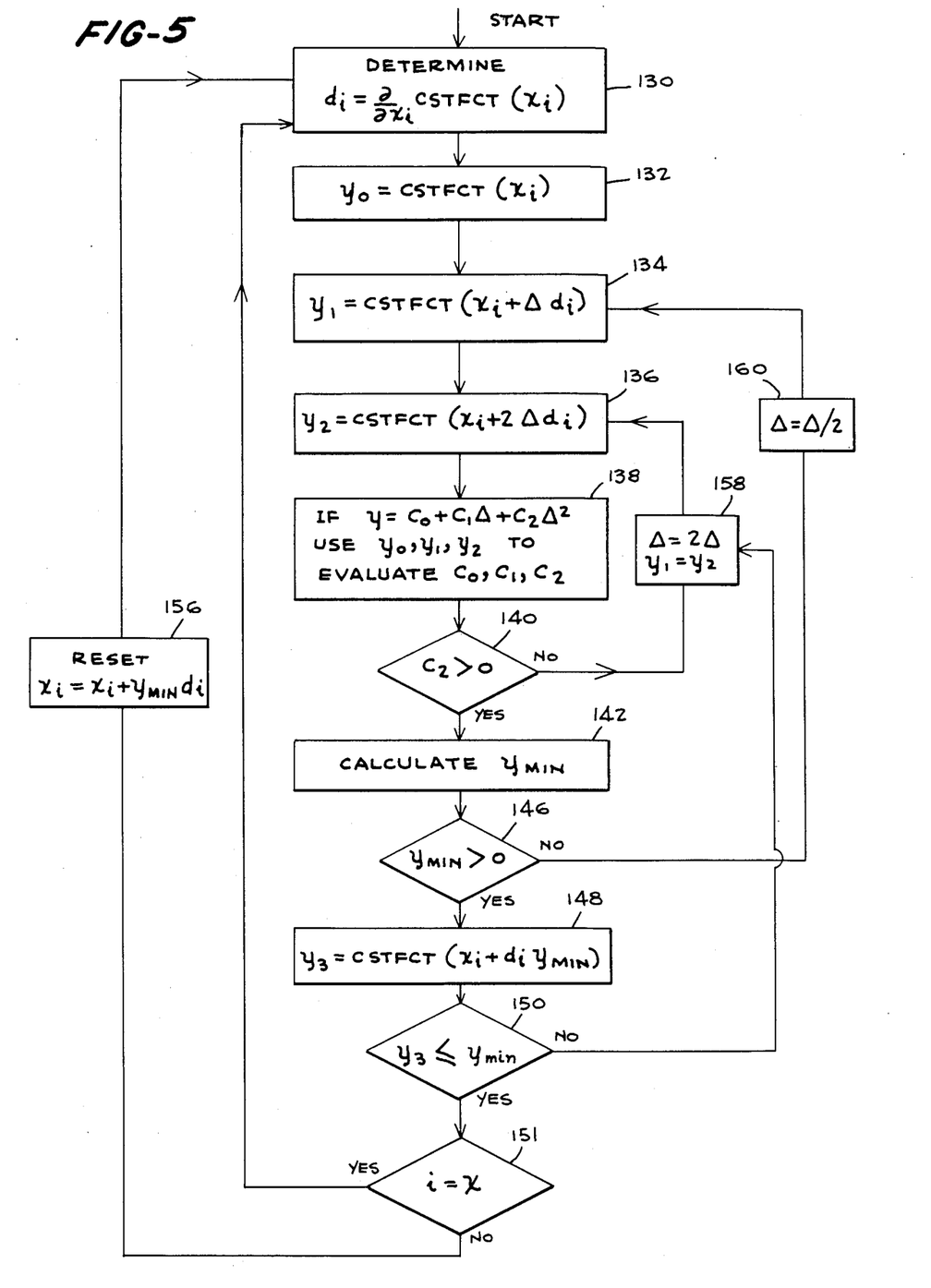
FIG. 5 is a flow diagram of a computer program for effecting a least means squared (LMS) operation on the control signal of single frequency to effect a minimization of the noise within the control volume of the aircraft as illustrated in any of FIGS. 1A, 1B, 2A, 2B, or 3 and as executed by the computer shown in FIG. 4A.

The gains of each of the amplifiers 56 and 58, as shown in FIG. 4B, are set in accordance with the calculation of a least means squared (LMS) program as executed in the computer 36, as shown in FIG. 4A. A flow diagram of the LMS program is shown in FIG. 5 and will be described below. By varying the gains of the amplifiers 56 and 58, the amplitude and the phase of each of the driver signals applied to the actuators 24a to 24n, is controlled. The illustrated program attempts to lower the system error as indicated by an error or cost function (CSTFCT), which is a quadratic function of its control variables, i.e. the gain of each of the amplifiers 56 and 58 as shown in FIG. 4B and represented as $x_i$. In the illustrative embodiment as shown in FIG. 4B, there is a single variable for the common gain of each of the amplifiers 56a to 56d and a separate variable for the gain of each of the phase setting amplifiers 58a to 58d for a total of five variables for each channel of the digital phase-gain circuit 38, realizing that there is one channel for each actuator 24. In the illustrative embodiment, where four actuators 24 are employed, a total of 20 variables would need to be set.

The cost or error function Y may be represented as follows:

$$Y = (\xi - \xi_{req.})^2 = \text{CSTFCT}(X_1, X_2 - X_i) \quad (3)$$

where $\xi$ is the signal provided by the spatial averaging circuit, and $\xi_{req}$ is the target error or minimum average noise that will be permitted within the control volume 10 of the aircraft's cabin 12. Y may be expressed as a parabola, where the control variables $X_i$ correspond to the gains of the amplifiers 56 and 58. The LMS program will find the minimum error $Y_{min}$ by varying one variable, i.e. the gain of one of the amplifiers 56 or 58, at a time by fitting this quadratic cost function to at least three measured points obtained by the measurement of the output signal $\xi$ of the spatial averaging circuit 34 and thereafter obtaining corresponding values of Y. By vector searching, the direction toward the minimum value or bottom of the cost function is established and three points on its parabolic curve are determined by stepping or providing set changes of the variables $X_i$. After the value of $Y_{min}$ for the cost function is determined, a corresponding control variable or gain $X_i$ is then set. The LMS program is fully described in the NASA Contractor Report 165698, entitled "An Operations Manual For The Spinning Mode Synthesizer In The Langley Aircraft Noise Reduction Laboratory" by Daniel L. Palumbo. Though the LMS program is not considered to be the protected invention of this document, it described in order to give a more complete understanding of this invention. The cost function Y may be expressed as follows:

$$Y = C_0 + C_1\Delta + C_2\Delta^2 \qquad (4)$$

$$\frac{\partial Y}{\partial \Delta} = C_1 + 2C_2\Delta \qquad (5)$$

$$\frac{\partial^2 y}{\partial \Delta^2} = 2C_2, \qquad (6)$$

where $\Delta$ is the preset step change of a particular variable or gain $X_i$ of one of the amplifiers 56 or 58, and $C_0$, $C_1$, and $C_2$ are coefficients, which will be determined by simultaneously solving the equations (4) to (6).

Referring now to FIG. 5, the LMS program will now be explained. When the program first starts up in step 130, an initial value is *assumed* for $\partial y/\partial \Delta$ from experience. After the first run through, the program calculates $\partial y/\partial \Delta$ from equation (5) using the previously determined values of $C_0$, $C_1$ and $C_2$ (from the last run through). Next in step 132, the gain of the corresponding amplifier 56 or 58 is set in accordance with the variable $X_i$, and initial value of Y is obtained by measuring the signal Y. In step 134, the value of the first variable $X_i$ is changed by a predetermined amount $\Delta d_i$ to provide a second value of the cost function $Y_1$. Similarly, in step 136, the variable $X_i$ is further incremented by the predetermined change $2\Delta d_i$ to derive a second value $Y_2$ of the cost function. The values of $Y_0$, $Y_1$ and $Y_2$ are entered into equation (4) to provide three equations, which are simultaneously solved in step 138 to provide values of $C_0$, $C_1$, and $C_2$.

Next, the program of FIG. 5 determines whether the quadratic equation fits the three previously determined values of the variable $X_i$ and, in particular, ascertains whether the third variable $X_i+2\Delta d_i$ falls on the other side of the minimum value $Y_{min}$ of the parabola from the variables $X_i$ and $X+\Delta d_i$. To that end, step 140 determines whether the calculated value of the coefficient $C_2$ is greater than 0. If the coefficient $C_2$ is less than 0 indicating that the predetermined value of $\Delta$ was selected too small, step 158 doubles the predetermined value of $\Delta$ and sets the value of the next $Y_1$ to be calculated as the previously calculated value $Y_2$ of the cost function, before step 136 recalculates the value of the cost function. If $C_2$ is greater than 0, indicating that a fit has been achieved, step 142 calculates the minimum value $Y_{min}$ of the parabola from the equations (4) to (6), their coefficients $C_0$, $C_1$, and $C_2$ having been calculated above in step 138. Step 146 tests the calculated minimum value $Y_{min}$ of the noise to determine whether it is greater than 0. If not, indicating that the preset value of the $\Delta$ is selected to be too large, step 160 takes a smaller value of the change $\Delta$ for the variable $X_i$ before returning to step 134 to attempt a further fit of the quadratic equation to the calculated points $X_1$, $X_2$, etc. However, if the calculated minimum value $Y_{min}$ is greater than 0, tending to indicate such a fit, step 148 further tests the cost function Y by measuring a value of $Y_3$ at a further incremental change of the control variable $X_i$ corresponding to the location of the minimum of the parabola. If the newly measured value of $Y_3$ is greater as indicated in step 150 than the previously calculated value of $Y_{min}$ indicating that the minimum has not yet been found, the program returns to step 158, whereby the change $\Delta$ of the variable is increased by two, before returning to step 136 to attempt a further fit.

If the value of $Y_3$ is equal to or less than $Y_{min}$, indicating that a fit has been achieved, step 151 determines whether all of the variables $X_i$ have been set and, if not, the program returns to step 130 to set the next variable $X_i$ or gain of one of the amplifiers 56 or 58. If all of the variables have been set, the program moves to step 156, which senses a change of the system's operating condition to continue execution of the program software under the new conditions, whereby a new change of $\Delta$ of the variable is set.

Figure 6:
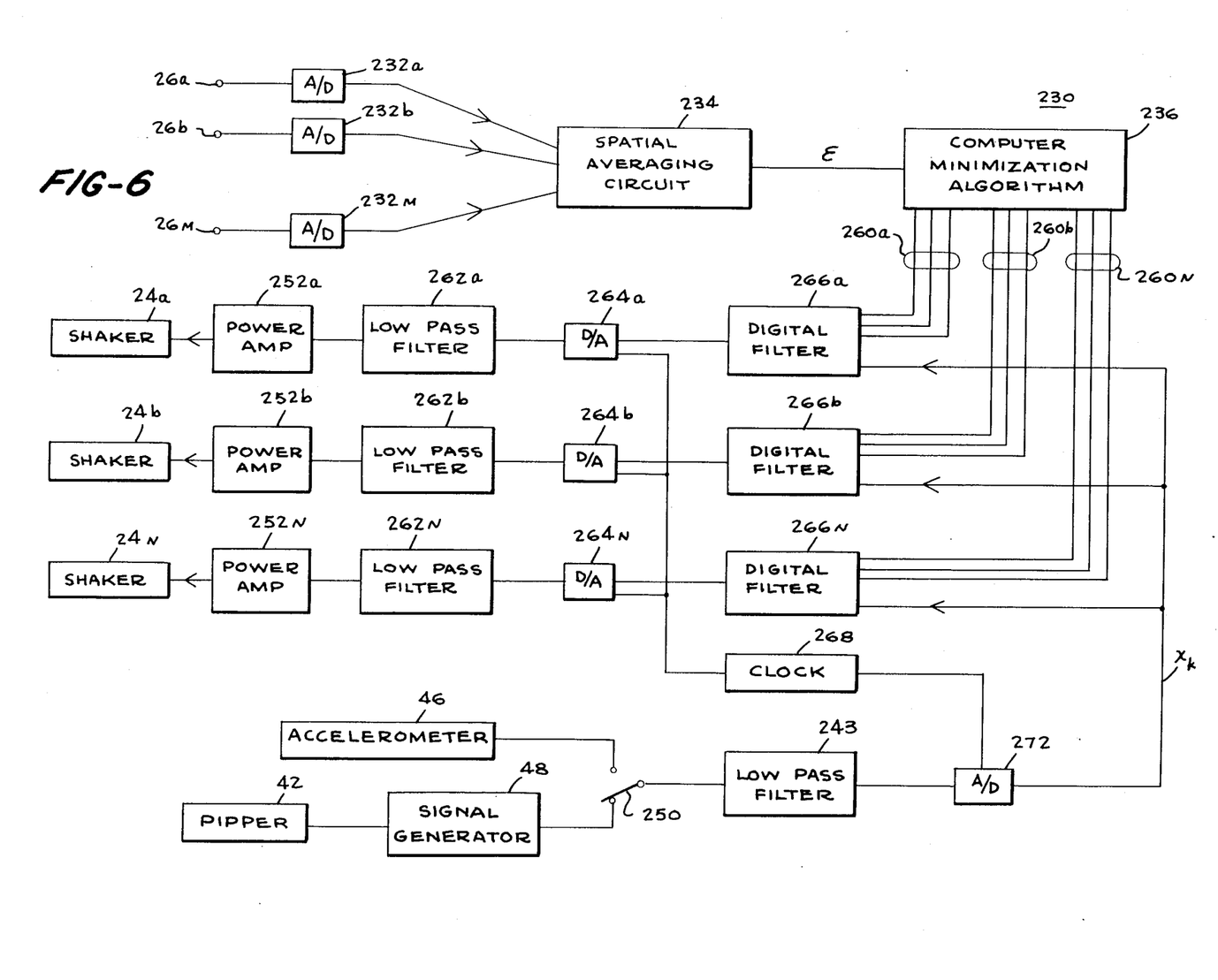
FIG. 6 is a functional block diagram of a further embodiment of the active noise reduction system for responding to a control signal including a plurality of or a band of propeller noise components.

Referring now to FIG. 6, an active noise reduction system 230 will be described for reducing noise of a plurality of noise frequencies or a broad band of noise, wherein similar elements are designated with like numerals but in the 200 series. In a manner similar to that of the first embodiment, an array of "m" microphones 26a to 26m senses the noise within the control volume 10 of the aircraft cabin 12 to provide a set of analog signals, which are converted by a corresponding set of A/D converters 232a to 232m to digital form. In turn, the resultant digital signals are applied to a spatial averaging circuit 234 for summing the input digital signals to provide a digital error signal $\xi$ indicative of the acoustic energy throughout the control volume 10. A control signal $X_k$ is developed by either the accelerometer 46 or the pipper 42 or exterior microphone. In a manner similar to that described above, the pipper 42 is coupled to sense the rotational velocity of the propellers 20 to provide a signal indicative thereof to the signal generator 48, which includes a plurality of oscillators, each oscillator outputting a signal indicative of selected of the harmonic noise frequencies. As indicated above, the harmonic frequencies may be determined from the rotational velocity of the propeller 20, as well as the number of propeller blades. The accelerometer could be replaced by a microphone disposed externally of the fuselage 14 to provide a signal indicative of the frequency noise content of the propellers 20 and the engines 18. The signal generator 48 sums the outputs of the plurality of oscillators and applies them via an aliasing filter 270 and A/D converter 272 to each of "n" digital filters 266a to 266n, where n corresponds to a number of actuators or shakers 24a to 24n. In a manner similar to that described above, the accelerometer 46 is connected externally to the fuselage 14 of the aircraft to sense principally the spectral content of the vibrations induced by the engine 18 and its propeller 20 to the fuselage 14 and into the aircraft cabin 12. The principle frequencies of this noise generally lie in a bandwidth of 50 to 500 Hz and frequencies above that level are filtered out by a low pass filter 243. This filtered signal is applied through the A/D converter 272 to each of the digital filters 266a to 266n. As will be discussed below, each of the digital filters 266a to 266n employs a plurality of coefficients or gains $w_i$ to determine the phase and amplitude of its output.

A computer 236 executes a suitable minimization algorithm such as the known Widrow-Hoff least means squared (LMS) algorithm to provide corresponding sets of coefficients via busses 260a to 260n to the digital filters 266a to 266n, respectively. As will be explained, the coefficients $w_i$ are set such that the digital output of each filter 266 controls the phase and amplitude of the signal to each actuator 24 in a manner to attenuate the noise within the control volume 10 to a predetermined level $\xi_{req}$. In particular, the digital outputs of the digital filters 266 are applied to digital-to-analog (D/A) converters 264, thus converting the filter outputs to analog form, before the outputs are filtered by low pass filters 262 to smooth their outputs, amplified by power amplifiers 252 and then applied to drive their respective actuators 24.

A clock 268 is coupled to each of the A/D converter 272 and to the D/A converters 264a to 264n, whereby the sampling rate of the noise error signal is selected. In accordance with the Nyquist criteria, the sampling rate (SR) must be at least twice that of the highest frequency of interest in order to accurately sample such information. Measurements indicate that the highest harmonic frequency of aircraft/propeller noise is typically below 500 Hz; therefore, in an illustrative embodiment of this invention, the clock 268 samples the A/D converter 272 and the D/A converters 264 at an illustrative sampling rate of 1,000 Hz.

Figure 7:
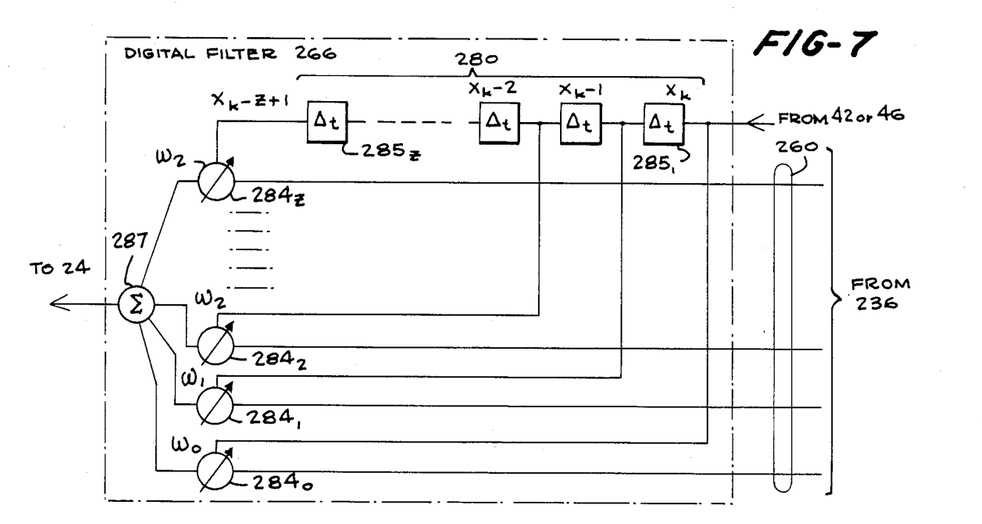
FIG. 7 is a detailed circuit diagram of the digital filter as incorporated within the functional block diagram of FIG. 6.

The digital filter 266, as incorporated into the active noise reduction system 230 of FIG. 6, is more fully shown in FIG. 7. The digital filter 266 illustratively comprises a series of "z" delay elements $285_1$ to $285_z$ to store and provide at one instant of time a set of "$z+1$" measurements $X_k$ to $X_{k-z+1}$, which are in turn applied to a corresponding set of multipliers $284_0$ to $284_z$. As explained above with respect to FIG. 6, the control signal $X_k$ as derived from either the pipper 42, the accelerometer 46 or an external microphone is sampled at a rate determined by the Nyquist Theory. The delay imparted by each of the delay elements 285 is set equal 1/SR, where SR is the sampling rate in terms of samples per second. For example, if the sampling rate SR of the A/D converter 272 is 1,000 samples per second, the delay imparted by each elements 285 is 1/1,000 or 1 millisecond.

The number "z" of samples (and thus the number of coefficients) determines the frequency resolution of the digital filters 266 in accordance with the following expression:

$$z = 2 \times \frac{\text{Total Signal Bandwidth}}{\text{Frequency Resolution}} \tag{7}$$

In turn, the frequency resolution is set considerably less than the smallest spacing between the noise frequencies of interest to ensure that all noise of interest is correctly sensed and processed. The A/D converter 272 samples the control signal $X_k$ and provides a sequence of the sampled control signals to the digital filters 266, where the sequence of sampled signals $X_k$, $X_{k-1}$, $X_{k-2}$-$X_{k-z+1}$ is stored by the series of "z" delay elements $285_1$ to $285_z$. Thus at any one instant of time, the series of delay elements 285 provides a "history" of the last $z+1$ sample control signals $X_k$ to $X_{k-z+1}$. The set of $z+1$ sample control signals are in turn applied to a corresponding set of multipliers $284_0$ to $284_z$ and are multiplied by corresponding weighing coefficients or gains $w_i$ as derived via the buss 260 from the computer 236. A corresponding set of multiplied samples is derived from the set of multipliers 284 and summed by a summing circuit 287 to provide a signal of selected amplitude and phase to drive its corresponding actuator 24.

Figure 8:
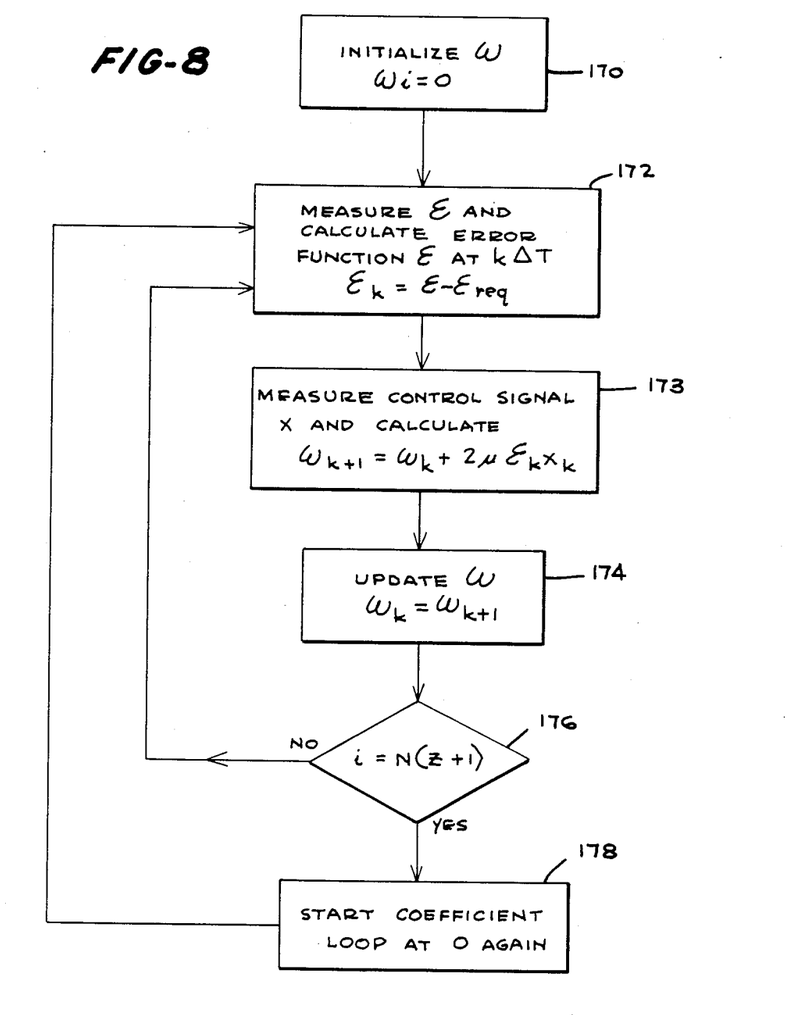
FIG. 8 is a flow diagram of a computer program executed by the computer shown in FIG. 6 to provide control signals for driving the actuators incorporated within any of the aircraft's shown in FIGS. 1A, 1B, 2A, 2B, or 3 in accordance with a minimization algorithm, whereby the noise within the control volume of the aircraft is minimized.

The Widrow-Hoff LMS algorithm as embodied in the computer software executed by the computer 236, is well known per se in the art as disclosed in "Adaptive Noise Cancelling: Principles and Applications," appearing in the *PROCEEDINGS OF THE IEEE*, Volume 63, number 12, December, 1975 by B. Widrow et al. and in U.S. Pat. No. 4,473,906 of Warnaka et al. An exemplary embodiment of such an LMS minimization algorithm will now be explained. Referring now to FIG. 8, there is shown a flow diagram executed by the computer 236 to calculate each of the weighting coefficients or gains $w_i$ as are loaded within each of the sets of multipliers 284 of the digital filters 266a to 266n. Initially in step 170, each of the weighting coefficients $w_i$ is set equal to 0. Next, beginning with the first weighting coefficient $w_o$ of the first digital filter 266a, the program sequentially calculates each of the weighting coefficients $w_i$. After initialization, step 172 calculates the error or cost function $\xi_k$ at the next time $k\Delta T$, by first sampling the current output $\xi$ of the spatial averaging circuit 232 and subtracting therefrom the value of the predetermined or required noise error $\xi_{req}$. Thereafter, the next weighting function $w_{k+1}$ is calculated in step 173 in accordance with the following equation:

$$w_{k+1} = w_k = 2\mu\epsilon_k X_k \tag{8}$$

where $w_k$ is the value of the last calculated weighting coefficient, $\mu$ is a scaling factor which controls the rate of convergence and stability of the algorithm, $\xi_k$ is the calculated error function as calculated in step 172 and $X_k$ is the sampled value of the control signal as derived from either the pipper 42 or the accelerometer 46 as sampled by the A/D converter 272 at time k. Next in step 174, the last value of the weighting function $w_{k+1}$ is transferred to the storage place for the previously calculated value of $w_k$. Then step 176 determines whether all of the weighting factors $w_i$ have been calculated, i.e. does the index "i" of the calculated weighting factor "w" equals n(z+1) corresponding to the total number of weighting factors "w" required for each of the digital filters 266 of the active noise reduction system 230. If not indicating that there are further weighting coefficients "w" to be calculated, the program returns to step 172, looping until all of the weighting coefficients "w" have been calculated. If all of the weighting coefficients "w" have been calculated, the program moves to step 178, which re-initializes the indicies of the weighting coefficients and tap delay elements in order to allow further minimization. In this form, the controller will run continually, first finding the minimum required ($\xi_{req}$) by adjusting the digital filter weighting coefficients and then responding to system changes. If so desired, a stop decision could be inserted to stop the system when $\xi_{req}$ is reached.

In an illustrative embodiment of this invention, wherein but a single actuator 24 is employed, the control circuit 236 and the digital filter 266 could take the form of that circuit manufactured by Digital Audio Corporation of Anaheim, Calif. under their designation DAC 10241.

Thus, there has been shown several embodiments of the active noise reduction system of this invention capable of reducing globally the level undesired noise within a control volume by 8 to 20 dB. Such noise reduction systems are particularly applicable to ATP aircraft, where prior art methods of noise reduction including passive means such as noise reducing panels, would have added undue weight to such aircraft and reduced their efficiency of performance. By contrast, the active noise reduction system of this invention employs a limited number of actuators coupled to a noise radiating surface, e.g. the aircraft fuselage, and driven as to amplitude and phase to attenuate the noise within the control volume to a predetermined level.

In considering this invention, it should be remembered that the present disclosure is illustrative only and the scope of the invention should be determined by the appended claims. Though the present disclosure has been directed toward describing an apparatus and method for global noise reduction of aircraft, it is understood that the present invention could be employed, without departing from the scope of this invention, to attenuate noise within other control volumes or environments.

I claim:

1. Apparatus for attenuating sound radiated from a vibrating surface intoa control volume surrounded by the vibrating surface, said apparatus comprising:
   (a) means for providing a control signal indicative of the frequency and amplitude of the sound radiated from said vibrating surface into said control volume;
   (b) vibrating means directly connected to said vibrating surface for further vibrating said vibrating surface to induce a cancelling sound into said control volume for combining with an attenuating said radiated sound;
   (c) detecting means disposed within said control volume for detecting the combination of said cancelling and said radiated sound to provide an error signal indicative thereof; and
   (d) control means responsive to said error signal for adaptively modifying said control signal as to phase and amplitude and for applying said modified control signal to drive said vibrating means, whereby said error signal is driven to a minimum level.

2. The sound attenuating apparatus as claimed in claim 1, wherein there is "n" number of efficient coupling modes between said vibrating surface and said control volume, where "n" may equal 1, and said vibrating means includes "n" actuators coupled to said vibrating surface.

3. The sound attenuating apparatus as claimed in claim 1, wherein said detecting means comprises a plurality of sound sensors disposed in an array defining said control volume.

4. The sound attenuating apparatus as claimed in claim 1, wherein a sound source emanates sound in a sound plane intersecting said vibrating surfce to define an intersecting line therewith, said vibrating means directly coupled to said vibrating surface at a point spaced a distance sufficiently close to said intersecting line to effectively attenuate said radiated sound.

5. The sound attenuating apparatus as claimed in claim 1, wherein there is included a housing including said vibrating surface, said housing enclosing said control volume and including a dimension defining the extent of said control volume, and a sound source for emanating sound along a sound plane intersecting said housing to define an intersecting line therebetween, said vibrating means including at least one actuator directly coupled to said housing at a point spaced from said intersecting line a distance less than said dimension to effectively attenuate the sound radiated into said control volume.

6. The sound attenuating apparatus as claimed in claim 5, wherein said detecting means comprises a plurality of sound sensors disposed in an array within said housing to define the extent of said control volume.

7. The apparatus of claim 1, wherein said modified control signal drives said vibrating means to vibrate said vibrating surface at predetermined frequencies to induce a cancelling sound for combining with and attenuating only those sounds that radiate into said control volume.

8. Apparatus for attenuating sound within an aircraft fuselage emanating from an aircraft engine, said aircraft engine transmitting sound along a sound plane intersecting said aircraft fuselage to define a circumferential line intersecting therewith, said fuselage enclosing and surrounding a control volume, said sound attenuating apparatus comprising:
   (a) means for providing a control signal indicative of the frequency and amplitude of the sound transmitted from aircraft engine through said vibrating fuselage and into said control volume;
   (b) vibrating means directly connected to said aircraft fuselage for vibrating said aircraft fuselage to induce a cancelling sound into said control volume for combining with an attenuating said transmitted sound;

(c) means disposed within said control volume for detecting the combination of said cancelling sound and said transmitted sound to provide an error signal indicative thereof; and (d) control means responsive to said error signal for adaptively modifying said control signal as to phase and amplitude and for applying said modified control signal to drive said vibrating means, whereby said error signal is driven to a minimal level and said transmitted sound within said control volume is minimized.

9. The aircraft sound attenuating apparatus as claimed in claim 8, wherein said detecting means comprises a plurality of sound sensors disposed within said fuselage for defining the extent of said control volume.

10. The aircraft sound attenuating apparatus as claimed in claim 8, wherein there is a limited number "n" of shell modes efficiently coupled between said fuselage and said control volume, where "n" may equal 1, and said vibrating means includes "n" number of actuators directly coupled to said fuselage.

11. The aircraft sound attenuating apparatus as claimed in claim 8, wherein there is a limited number "n" of shell modes efficiently coupled between said fuselage and said control volume, where "n" may equal 1, and said detecting means includes a plurality of "m" microphones, where "m" equals 2 "n".

12. The aircraft sound attenuating apparatus as claimed in claim 8, wherein said fuselage has a cross-sectional diameter, and said vibrating means is directly coupled to said fuselage at a point spaced a distance not greater than said fuselage diameter from said intersecting line.

13. The aircraft sound attenuating apparatus as claimed in claim 8, wherein said sound sensing means comprises a sensor engaged on the outside of said fuselage with respect to said control volume for sensing the vibration induced by said aircraft engine in said fuselage for providing said control signal indicative thereof.

14. The aircraft sound attenuating apparatus as claimed in claim 8, said aircraft engine rotatably drives a propeller at a varying rotational velocity, said aircraft propeller defining a propeller plane along which the sound emanates therefrom into said fuselage defining a circumferential line intersecting therebetween, said sound sensing means responsive to the propeller noise for providing said control signal indicative thereof.

15. The aircraft sound attenuating apparatus as claimed in claim 14, wherein said sound sensing means is responsive to the rotational velocity of said aircraft propeller to provide said control signal indicative thereof.

16. The aircraft sound attenuating apparatus as claimed in claim 14, wherein said sound sensor provides said control signal of a fundamental frequency proportional to the velocity of said aircraft propeller and of the number of blades of said aircraft propeller.

17. The aircraft sound attenuating apparatus as claimed in claim 16, wherein said sound sensing means further includes means responsive to said control signal of said fundamental frequency for further generating and combining together "n" signals of higher harmonics of said fundamental frequency, where "n" may equal 1.

18. The aircraft sound attenuating apparatus as claimed in claim 8, wherein said control means comprises means for adjusting the phase and amplitude of said control signal for driving said vibrating means and a computer responsive to said error signal for executing a minimization program to control the phase and amplitude adjustment of said control signal.

19. The aircraft sound attenuating apparatus as claimed in claim 18, wherein said vibrating means comprises a plurality of "n" actuators coupled to said fuselage, said control means for dividing said control signal into "n" control signals and controlling the phase and amplitude of each of said "n" control signals.

20. The aircraft sound attenuating apparatus as claimed in claim 18, wherein said minimization program effects a Widrow-Hoff least mean square algorithm.

21. The apparatus of claim 8, wherein said aircraft engine exhibits a plurality of dominant frequencies, each of said frequencies causing at least one radiating shell mode within said vibrating surface, said shell mode being of the type radiating sound into said control volume, and said vibrating means operative to attenuate each of said radiating shell modes.

22. Apparatus for attenuating noise radiated from a vibrating surface as a radiated noise field at least partially surrounded by said vibrating surface, said apparatus comprising:

(a) means for providing a control signal indicative of the frequency and amplitude of the noise within said radiated noise field;

(a) vibrating means directly connected to said vibrating surface for further vibrating said vibrating surface to induce a cancelling sound into said radiating noise field for combining with and attenuating said radiated noise;

(c) a plurality of sensors disposed in an array defining a control volume within said radiation noise field, each sensor for detecting the combination of said cancelling sound and said radiated noise to provide an error singal indicative thereof; and (d) control means responsive to said error signal for adaptively modifying said control signal as to phase and amplitude and for applying said modified control signal to drive said vibrating means, whereby said error signal is driven to a minimum level and said noise within said control volume is attenuated.

23. The noise attenuating apparatus as claimed in claim 22, wherein said array of sound sensors defines a perimeter of said control volume.

24. The noise attenuating apparatus as claimed in claim 22, wherein said noise comprises a standing wave of a maximum frequency and having a given spacing between a pair of adjacent nodes thereof, wherein adjacent sensors of said array are spaced from each other a distance substantially equal to said given spacing.

* * * * *

UNITED STATES PATENT AND TRADEMARK OFFICE
CERTIFICATE OF CORRECTION

PATENT NO. : 4,715,559
DATED : December 29, 1987
INVENTOR(S) : Christofer R. Fuller It is certified that error appears in the above-identified patent and that said Letters Patent is hereby corrected as shown below:

Column 1, line 4, insert the following:

--This invention was made with Government support under contract NAG-1-390 awarded by NASA. The Government has certain rights in this invention.--

Signed and Sealed this

Fourth Day of October, 1988

*Attest:*

DONALD J. QUIGG

*Attesting Officer*      *Commissioner of Patents and Trademarks*